(12) United States Patent
Gorsuch

(10) Patent No.: US 6,561,996 B1
(45) Date of Patent: May 13, 2003

(54) APPARATUS AND METHOD FOR IN VIVO HEMODIALYSIS

(75) Inventor: Reynolds G. Gorsuch, Yountville, CA (US)

(73) Assignee: Transvivo, Inc., Napa, CA (US)

( * ) Notice: Subject to any disclaimer, the term of this patent is extended or adjusted under 35 U.S.C. 154(b) by 0 days.

(21) Appl. No.: 09/081,883

(22) Filed: May 19, 1998

(51) Int. Cl.[7] ............................................. A61M 37/00
(52) U.S. Cl. .................... 604/6.09; 604/4.01; 604/5.01; 604/5.04; 604/6.16; 604/28; 604/507; 128/898
(58) Field of Search .................. 604/4, 5, 6, 27–29, 604/890.1, 891.1, 892.1, 48, 507–508, 540, 4.01, 6.09, 5.01–5.04, 6.16, 39.41, 43, 44; 623/11, 12; 422/44, 48; 128/DIG. 13, 898–899

(56) References Cited

U.S. PATENT DOCUMENTS

| | | | | |
|---|---|---|---|---|
| 3,730,183 A | * | 5/1973 | Goldsmith et al. ......... 128/213 |
| 3,878,564 A | | 4/1975 | Yao et al. ........................... 3/1 |
| 4,265,249 A | | 5/1981 | Schindler et al. |
| 4,382,445 A | | 5/1983 | Sommers ........................ 604/8 |
| 4,416,657 A | * | 11/1983 | Berglund ........................ 604/9 |
| 4,493,696 A | | 1/1985 | Uldall ........................... 604/43 |
| 4,552,552 A | | 11/1985 | Polaschegg et al. ............ 604/4 |
| 4,694,832 A | * | 9/1987 | Ungerstedt ................... 128/632 |
| 4,708,713 A | * | 11/1987 | Lentz ............................. 604/5 |
| 4,718,890 A | * | 1/1988 | Peabody ........................ 604/29 |
| 4,769,037 A | | 9/1988 | Midcalf ........................ 623/12 |
| 4,898,669 A | | 2/1990 | Tesio ........................... 210/232 |
| 4,950,224 A | | 8/1990 | Gorsuch et al. |
| 5,002,054 A | | 3/1991 | Ash et al. ..................... 128/635 |
| 5,053,023 A | | 10/1991 | Martin ......................... 604/280 |
| 5,151,082 A | * | 9/1992 | Gorsuch et al. ................. 604/4 |
| 5,152,743 A | | 10/1992 | Gorsuch et al. |
| 5,224,926 A | | 7/1993 | Gorsuch et al. |
| 5,300,086 A | | 4/1994 | Gory et al. ................... 606/200 |
| 5,308,315 A | * | 5/1994 | Khuri et al. .................... 604/4 |
| 5,605,627 A | * | 2/1997 | Carlsen et al. ......... 210/321.79 |
| 5,615,671 A | * | 4/1997 | Schoonen et al. ........... 128/632 |
| 5,706,806 A | * | 1/1998 | Kissinger ..................... 128/632 |
| 5,735,809 A | | 4/1998 | Gorsuch ........................ 604/4 |
| 5,755,790 A | | 5/1998 | Chevillon et al. ............ 623/12 |
| 5,785,700 A | | 7/1998 | Olson .......................... 604/408 |

FOREIGN PATENT DOCUMENTS

| | | |
|---|---|---|
| FR | 2 398 507 | 7/1978 |
| WO | WO 96/14889 | 5/1996 |
| WO | WO 98/16171 | 4/1998 |

* cited by examiner

Primary Examiner—Angela D. Sykes
Assistant Examiner—Patricia Bianco
(74) Attorney, Agent, or Firm—Knobbe, Martens, Olson & Bear, LLP

(57) ABSTRACT

A method of removing toxins from a patient's blood comprises implanting a filter device having a dialysis membrane with an exterior surface exposed to the patient's blood and a dialysate cavity exposed to an interior surface of the dialysate membrane within a blood vessel of a patient, continuously directing substantially uncontaminated or substantially decontaminated dialysate into the dialysate cavity and in diffusive communication with the patient's blood, dialysing the patient's blood with the dialysate, and continuously removing toxin contaminated dialysate from the filter device.

74 Claims, 6 Drawing Sheets

APPARATUS AND METHOD FOR IN VIVO HEMODIALYSIS

BACKGROUND OF THE INVENTION

Treatment for acute kidney failure and chronic end stage renal disease is accomplished by various forms of continuous ambulatory peritoneal dialysis and hemodialysis, presently the most commonly used form of therapy. In all current hemodialysis procedures, blood is periodically removed from the patient's body, dialyzed ex-vivo and the treated blood returned to the body. Single patient conventional hemodialysis procedures are performed at an out-patient center 2 or 3 times a week in 3 to 4 hour sessions during which the patient's blood toxins are removed by dialysis and filtration to eliminate the toxins generated by the body during the 3 or 4 day period preceding the hemodialysis, and during the time the treatment is carried out. Thus, unlike normal kidney function in which dialysis is carried out continuously, the hemodialysis creates non-uniform toxin removal with "peaks and valleys" of toxin concentrations. Moreover, during the time that the toxins are above normal, the patient feels ill and the consequent buildup of fluid volume in the body caused by lack of urination results in a severe volume load on the right heart stressing an already compromised cardiovascular system, as well as creating an imbalance in the electrolyte system of the blood. During the hemodialysis, blood is pumped from the body and through a dialyzer cartridge at a high flow rate and simultaneously fluid is removed from the blood by ultrafiltration to reduce the blood volume to normality. The resulting procedure causes a massive change in blood hemodynamics in a short period of time and produces additional heavy stress on the human system with severe fluctuations in blood pressure and trauma to other body organs. Yet another serious problem is the persistent and periodic clotting of the blood in the inner lumens of the dialyzer even though the patient is anticoagulated with drugs such as heparin. The aforesaid current hemodialysis procedures are performed on over 600,000 patients per year in the United States alone at an expense to the healthcare system of over twelve billion dollars per year.

In U.S. Pat. Nos. 4,590,224, 5,151,082, 5,152,743, 5,224,926 and 5,735,809 there are disclosed methods and apparatus for in vivo separation of plasma from blood utilizing one or more hollow elongated microporous fibers implanted within a patient's blood vessel. The fibers are made of a microporous polymeric fiber membrane material having a pore size sufficient to allow diffusion of plasma into the hollow fiber interior but preventing cellular components larger than plasma to diffuse, ultrafiltrate or enter the fiber interior. The fiber or fibers are implanted within the blood vessel without significantly obstructing fluid flow through the vessel while providing the aforesaid in vivo plasma separation. The fiber assembly is secured in fluid communication with a catheter, preferably a dual lumen catheter having a first tube permitting plasma passage from the fiber and a second tube for returning plasma to the blood vessel after treatment. Various configurations and methods of fabrication as well as materials having a variety of characteristics and performance abilities are disclosed in the aforesaid patents and application as are various systems, apparatus, components and methods for use including measurement of blood parameters, kidney dialysis, and separation and removal of a substantial number of specific materials and plasma components, the descriptions of which are incorporated herein by reference. By continuously extracting plasma from the blood in-vivo and dialyzing only the plasma ex-vivo eliminates many of the failings of the present hemodialysis systems and procedures.

SUMMARY OF THE INVENTION

The present invention is intended to provide further improvement in removing toxins from a patient's blood. In the present invention, all of the function of kidney dialysis therapy can be performed continuously in-vivo and in-situ without removing from the body any blood, plasma or blood components except the toxins and other undesirable elements to be eliminated, thus substantially emulating the natural kidney.

In the present invention, a filter device comprising a dialysis membrane is implanted within the superior vena cava. The filter device includes a dialysate cavity which is exposed to the interior surface of the dialysis membrane, with the exterior dialysis membrane surface exposed to the patient's blood within the blood vessel. The filter device is secured at the end of a multiple lumen catheter through which dialysate fluid is continually directed. Conventional dialysate fluid, comprising sterilized water and desirable amounts of electrolytes and /or osmotic materials, well known to those skilled in the art, may be used. The dialysate fluid passing into the dialysate cavity of the filter device is in direct diffusive communication with the patient's blood to perform the dialysis function, and the resulting toxin-contaminated dialysate is removed from the filter device through a second catheter lumen. The filter device may also include an ultrafiltration cavity whereby the dialysate is in direct convective communication with the blood to produce an ultrafiltration function. Using such a device results in the blood and plasma dialyzed in place, and excess fluids extracted within the body whereby neither blood nor plasma need be removed from the patient's body. The invention also includes apparatus and systems as well as different configurations and embodiments of filter devices used in the process of the invention. Such methods and apparatus as well as the advantages will be disclosed in the following detailed description.

DETAILED DESCRIPTION OF THE INVENTION

The method of the present invention comprises removing toxins from a patient's blood utilizing a dialysis filter device implanted in a patient's blood vessel, preferably the vena cava. The exterior surface of the dialysis membrane element is in direct contact with the blood flowing through the patient's vein or vena cava. The interior surface of the dialysis membrane is exposed to dialysate fluid which flows continuously from an ex-vivo dialysate reservoir via a double or triple lumen catheter. One lumen of the catheter is for directing the dialysate fluid continuously into the dialysate cavity of the filter device and another lumen of the catheter is for returning the dialysate fluid to a collection bag. As the dialysate passes through the dialysis membrane, it is in direct diffusive communication with the blood to carry out the dialysis function. Thus, the blood and plasma are dialyzed in place and whereby neither blood nor plasma need to be removed from the body for removal of blood toxins. The dialysis membrane also acts as an ultrafilter with the dialysis fluid in direct convective communication with the blood to perform an ultrafiltration function with excess fluids also extracted and removed from the patient via the dialysis filter.

The dialysis membrane filter used in the filter device may be microporous hollow fiber dialysis membrane or sheet dialysis membrane, various configurations and examples of which will be described hereinafter. The important and unique feature of the present invention is in using dialysis membranes for in-vivo dialysis as opposed to plasma separation membranes as disclosed in the aforesaid patents and applications. In the aforesaid methods and apparatus, the patient's blood is outside or exterior of the plasma membranes or fibers while the extracted plasma passes through the membranes to the inside of the filter device and is removed from the patient for treatment, and then returned. In the present invention the patient's blood, including the plasma, remains outside of the dialysis membrane and only the dialysate is inside the dialysis cavity of the filter device. The dialysis cavity is formed or defined interiorly of the dialysis membrane structure.

Figure 1:
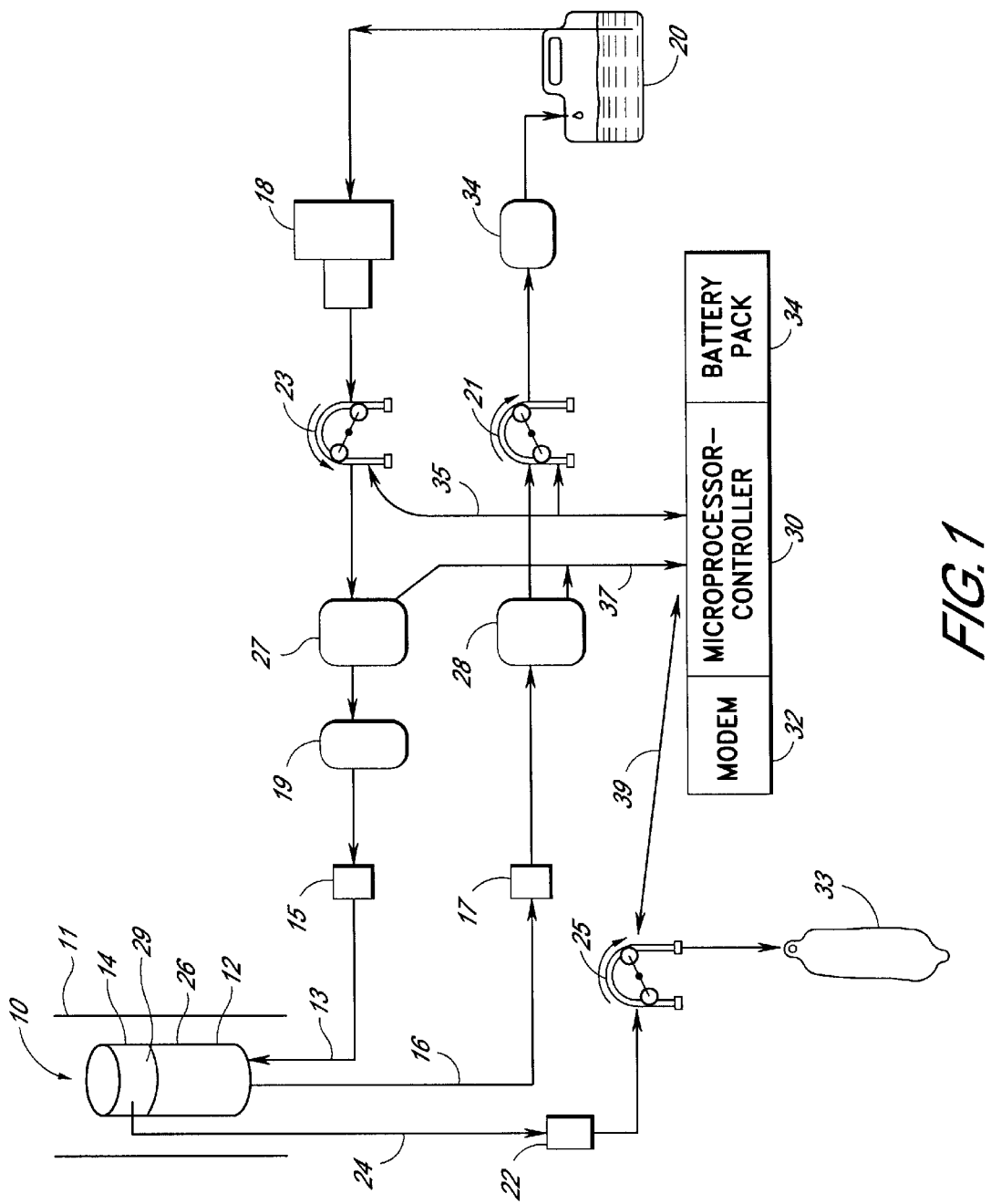
FIG. 1 is a schematic illustration of a system and apparatus used in the in-vivo hemodialysis process of the invention.

FIG. 1 illustrates a system for in-vivo hemodialysis according to the present invention designed primarily for ambulatory and home care applications where precision control of operating parameters is required. The system is intended to minimize the weight and bulk to be carried by the patient. In the system shown a triple lumen catheter is used with a filter assembly 10 which is transplanted into the patient's superior vena cava 11 via the jugular vein. Percutaneous procedures for implanting the catheter and filter assembly are well known to those skilled in the art. Positioning of the filter assembly within the patient's vascular system are generally illustrated in U.S. Pat. Nos. 5,735,809 and 5,968,004, the descriptions of which are incorporated herein by reference.

In the system illustrated in FIG. 1, two separate filter devices are used, one for ultrafiltration and another for hemodialysis. The ultrafiltration filter device includes an ultrafiltration membrane 14 while the hemodialysis filter device uses a dialysis membrane 12. The ultrafiltration membrane 14 defines an ultrafiltration cavity 29 which is in communication with an ultrafiltration pump 25 via a catheter lumen 24. Interiorly of dialysis membrane 12 is a dialysate cavity 26 in communication with catheter lumens 13 and 16 for directing dialysate to and from the dialysate cavity, respectively. Fresh or relatively toxin uncontaminated dialysate is pumped to the filter device from a dialysate source which provides substantially uncontaminated or substantially decontaminated dialysate fluid. Thus, the dialysate supplied to the filter assembly may be fresh, unused dialysate, or from a decontaminated and filtered dialysis source as is illustrated. Any suitable barrier for separating the two cavities may be used.

The ultrafiltration function in the system illustrated is used for weight control for drawing fluid from the patient's blood through the ultrafiltration membrane 14 in a controlled manner by ultrafiltration pump 25 via third catheter lumen 24. The ultrafiltrate is discharged into a waste bag 33 for periodic disposal. A pressure transducer 22 is also used to monitor the pressure within lumen 24, with communication link 39 directing control signals from the microprocessor-controller 30 to and from the ultrafiltration pump 25.

The physical structure of the ultrafiltration and dialysis filter devices may be the same or different. Thus, each filter may use one or the other of the types of filter devices or assemblies of the aforesaid patents or applications incorporated herein by reference, or one of the filter assembly configurations disclosed hereinafter. However, the membranes used in the respective filters have different sieving coefficient curves, permitting selective control of exudate over a wide or narrow band of particle sizes or molecular weights. The pore sizes for the ultrafiltration membrane are greater than those used for the dialysis membrane. Typically the ultrafiltration membrane will have a pore size or cut-off to allow passage of blood and plasma components of up to about $5.8 \times 10^4$ daltons. The dialysis membrane used has a low flux dialyser cut-off of about $5 \times 10^3$ and a high flux cut-off of about $5 \times 10^4$ daltons. A comparison of the blood and plasma components passing through these respective dialysis and ultrafiltration (hemofilter) membranes is further shown in Table I of U.S. Pat. No. 5,980,481, and incorporated herein by reference.

As shown in FIG. 1, dialysate to be used in the in-vivo hemodialysis is directed from dialysate bag 20 to a dialysate pump 23 and via inlet catheter lumen 13 to the dialysate cavity 26 of the filter assembly 10. A toxin absorption cartridge 18 may be used for decontaminating dialysate fluid as may be bacteria filters 15 and 17. Dialysate directed into dialysate cavity 26 is in direct diffusive communication with the blood flowing in vena cava 11. The major toxins present in the blood are low molecular weight nitrogenous compositions, primarily uric acid, urea and creatinine. The dialysate traverses the dialysis membrane element and absorbs the toxins by diffusion from the blood. The toxin contaminated dialysate then enters the return lumen 16 of the multiple lumen catheter where it is pumped via pump 21 to the dialysate bag 20. In the preferred embodiment, pressure tranducers 27 and 28 communicate with the inlet and return catheter lumens for sensing the pressure of the dialysate within the respective lumens. In yet another preferred embodiment, the system is controlled by a microprocessor-controller 30 which receives signals from the pressure transducers via communication link 37 and sends control signals via link 35 to the respective pumps 23 and 21. Thus, the controller 30 manages the system through monitoring of the flows in the lumens of the catheter for directing dialysate flow to and from the dialysis filter membrane 12. A modem 32 is also preferably used for communicating the system operations and parameters to a healthcare personnel or physician via a communication line. The microprocessor-controller may be powered by a battery pack 34.

Other optional features of the system illustrated include a blood urea nitrogen (BUN) sensor 34 positioned along the return catheter 16 between the pump 21 and dialysate bag 20. The urea nitrogen content of the patient's blood is monitored by such a sensor, with information sent to the microprocessor-controller for further management of the system and for operating the pumps. The microprocessor-controller may calculate patient's needs based on the protocol entered into the apparatus by a physician. The differential pressure across ultrafiltration membrane 14 may also be detected to determine the flow rate of plasma in the ultrafiltration circuit. The operation of pumps 21 and 23 determine the flow rate of the dialysate circuit and also regulate a neutral differential pressure across the dialysis membrane 12. Patient protocol commands may be downloaded by a physician via modem 32 as may operating system parameters reported to the physician or caregiver. A bubble sensor 19 may also be used. Other controllable variables affecting system performance will depend on composition, morphology, design and size of the ultrafiltration and dialysis membranes as well as the flow rate of the dialysate in the dialysis circuit.

Figure 2:
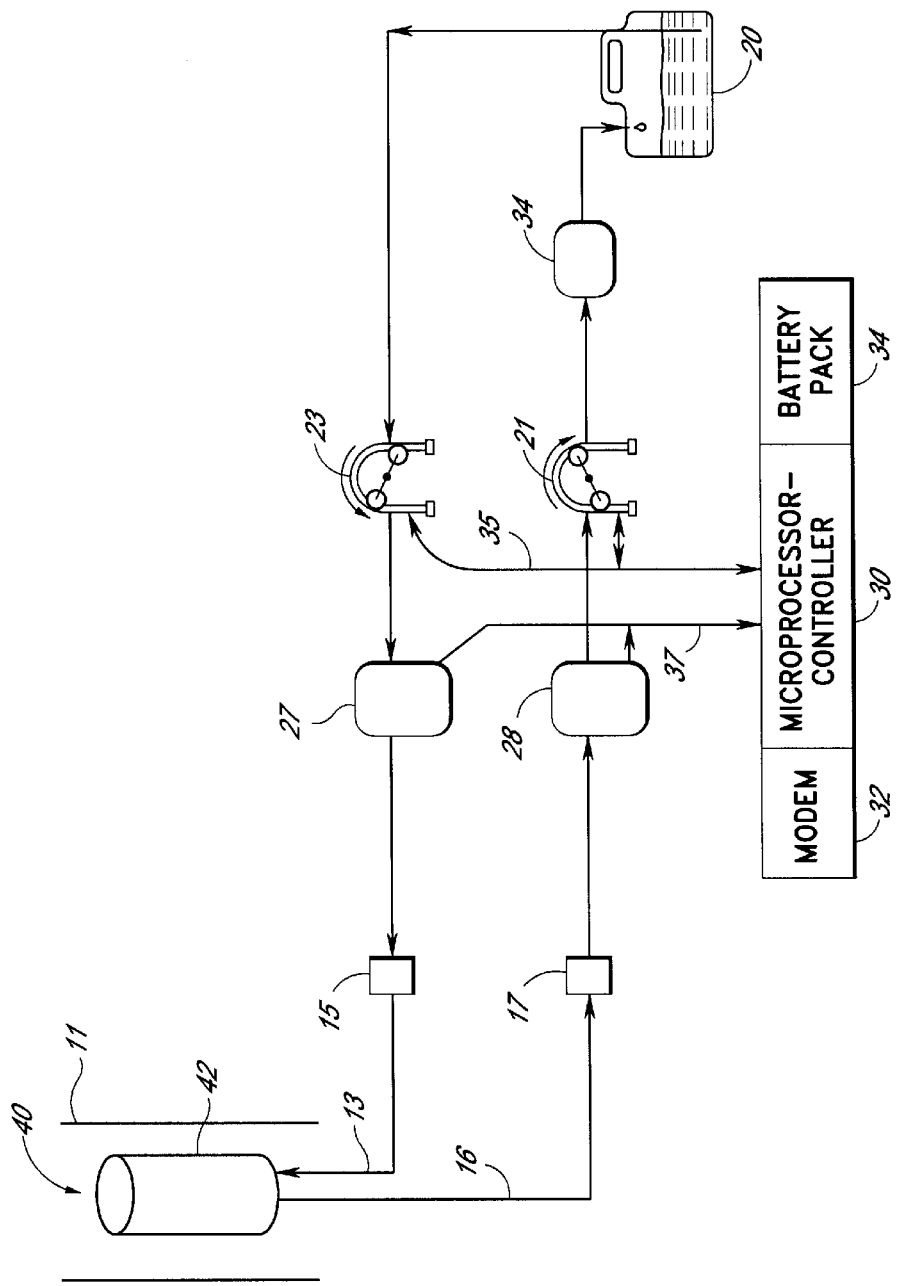
FIG. 2 is a schematic illustration of an alternative system of the invention used for in-vivo hemodialysis.

FIG. 2 illustrates an alternative system configuration similar to that of FIG. 1 but designed for use in acute care and in dialysis center facilities where dialysate is in plentiful supply and need not be carried or transported by the patient. In the system illustrated, the dialysate filter device 40 is used only with a dialysate membrane 42, whereby a separate ultrafiltration filter and the optional toxin absorption cartridge are omitted with ultrafiltration accomplished by the dialysis membrane without using a separate ultrafiltration membrane and cavity. In the system shown, the exudate accumulated in the dialysis bag 20 is discarded when the dialysate is saturated with toxins to an unacceptable level and is to be replaced. Thus, the dialysate may be recirculated to the filter device for continued diffusive communication with the patient's blood until a pre-established toxin level has been detected. The system may be provided with a sensor for sensing the toxin limit in the dialysate with an appropriate alarm or other means for signaling the time for discarding the toxin laden dialysate and replacing it with fresh dialysate.

Figure 3:
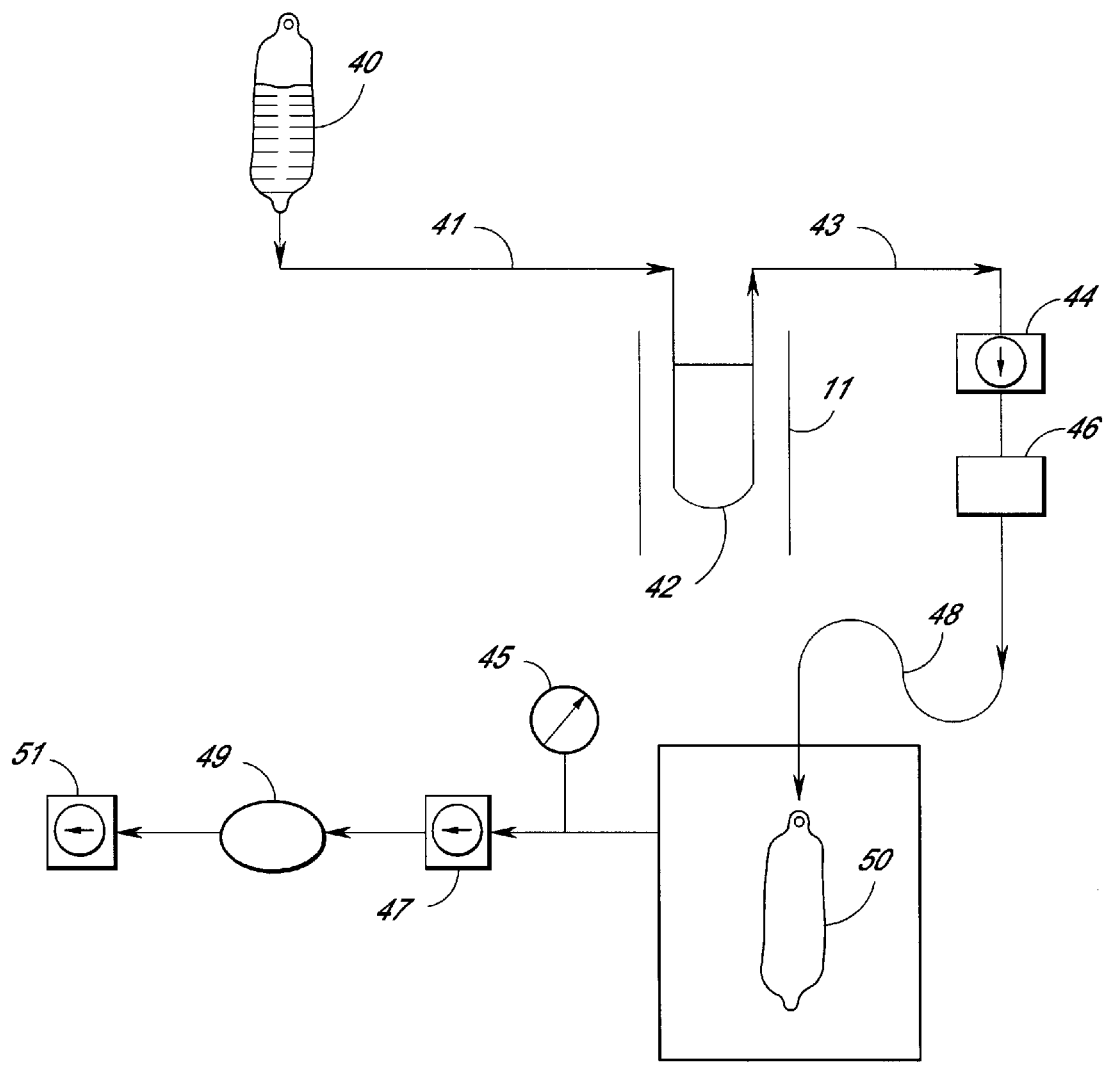
FIG. 3 is a schematic illustration of a simplified system for in-vivo hemodialysis according to the invention.

FIG. 3 illustrates a simplified system used for in-vivo hemodialysis according to the invention. Such a system, although having limited application, is economical and most cost effective. The system shown has no powered pumps, electrical devices, computers or other expensive components and operates on gravity, with adjustable flow control mechanisms including a hand-powered vacuum pump. Preferably, all components are completely or semi-disposable.

The system shown includes a dual lumen catheter having an inlet lumen 41 and an outlet lumen 43 for directing dialysate fluid to and from dialysis filter membrane element 42, respectively. The filter element is surgically implanted in the superior vena cava via the internal jugular vein using conventional permacath-type bacterial cuffs for bacterial seal as known by those skilled in the art. A dialysate bag 40, for example, a 1.5 liter graduated bag, is worn over the patient's shoulder just below the neck and above the patient's heart, preferably against the patient's skin. The dialysate bag is connected to the in-flow lumen of the dialysis catheter via a control device and bacteria filter, not shown. The gravitationally-fed dialysate fluid flows through the input catheter lumen and into the dialysate cavity of the dialysis filter device 42. The filter device and the dialysis operates substantially as previously described with the dialysate communicating with the blood by diffusive means for dialysis and by convective means for ultrafiltration. Dialysis is driven by the difference in toxin concentration between the blood and the dialysate. The driving force for ultrafiltration is the differential pressure across the dialysate membrane generated by the positive head of the dialysate bag and the negative pressure generated in the outflow lumen of the catheter 43 by the siphon and vertical distance between a drain bag 50 and the dialysate bag 40. Output lumen 43 of the catheter is connected via another bacteria filter, not shown, and one-way or check valve 44 to a collection bag 50. A siphon column tubing communicating between the outflow catheter lumen 43 and the drain bag 50 includes a mechanical flow control valve 46 and a siphon lock device 48, formed by a vertically oriented tubing loop. If operation of the system requires additional negative pressure across the dialysis membrane for ultrafiltration, or where it is inconvenient or difficult to maintain an adequate vertical distance between the dialysate and drain bags, a manual vacuum means which can be squeezed by the patient's hand, such as a rubber bulb 49, in combination with one-way check valves 47 and 51 may be used. A mechanical vacuum gauge 45 may also be incorporated for observing the amount of pressure created by the hand-squeezed vacuum ball. It may also be desirable to use substantially identical dialysate and drain bags for readily detecting when all of the dialysate has passed from the dialysate bag to the drain bag, and allowing the bags to be conveniently interchanged if the protocol requires several passages of the dialysate prior to disposal and replacement.

The system and apparatus shown in FIG. 3 may be most effectively used for patients weighing less than about 100 kg and having some residual renal function and relatively low protein intake diet thus requiring less than about 15 liters per day of plasma urea clearance, equivalent to that achieved by peritoneal dialysis systems. Such patients represent a rather large portion of the patient population and do not require additional nighttime dialysis treatments. The aforesaid system may also be advantageously used where healthcare costs are critical to the patient and/or the healthcare system which provides the apparatus.

Figure 4:
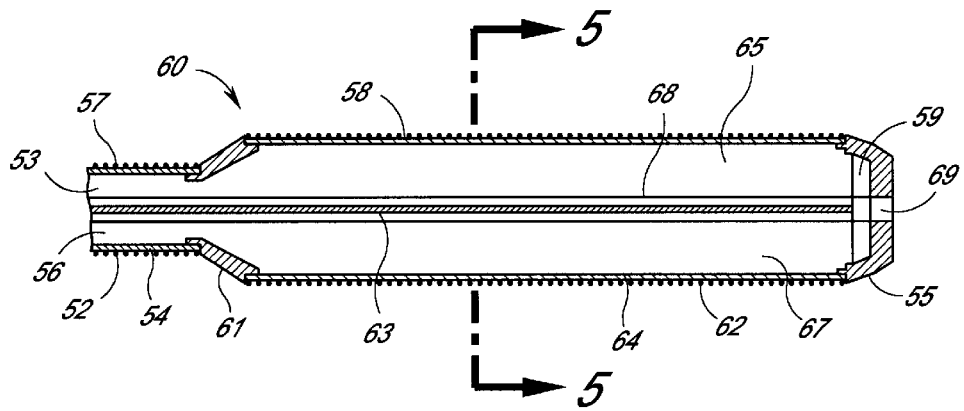
FIG. 4 is a side sectional view of a filter device of the invention in the form of coaxial tubes using dialysis membrane sheets.
Figure 5:
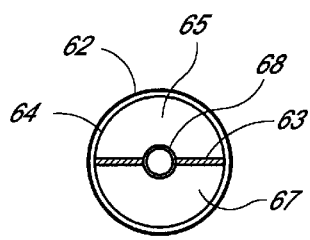
FIG. 5 is a sectional view of a tube filter device of FIG. 4 taken along lines 5—5.

FIG. 4 illustrates a dialysis filter device configuration utilizing two tubes of dialysis sheet membrane having different diameters. Such a device may be advantageously used to accommodate the central proximal portion of the vena cava and a more distal portion of that vein close to the junction of feeder veins such as the subclavean and/or the jugular vein. By using smaller diameter assemblies, a larger surface area of total dialysis membranes is achieved. The device shown comprises a filter element 60 having a smaller diameter tube 57 coaxially mounted to a larger diameter tube 58 using a header 61. The filter device is secured to the end of a multiple lumen catheter having an inlet lumen for communicating with inlet passageway 53 and outlet lumen for communicating with outlet passageway 56 of the smaller diameter tube 57. Larger diameter tube 58 includes an inlet passageway 65 and an outlet passageway 67 and an end or terminal header 55. Observing also FIG. 5, a lumen separator panel 63 extends along the length of both smaller and larger diameter tubes for separating the inlet and outlet passageways. The filter device shown uses a sheet of dialysis membrane. The smaller tube 57 is wrapped with a membrane sheet 52 and the larger tube 58 with a membrane sheet 62. Membrane support members are used along the respective small and larger diameter tubes to support the membrane sheets. The dialysis membranes are quite thin, typically between 10 and 30 μm, thus having little structural strength. The small diameter support 54 and large diameter support 64 provide for such a function. In the embodiment shown, a third lumen 68 is provided for infusing drugs and/or nutritional fluids or to provide means for sampling blood for lab analysis. The third lumen communicates exterially at port 69 at the end of terminal header 55. The terminal header includes a cavity 59 communicating the dialysate inflow and outflow lumens 65 and 67.

Figure 6:
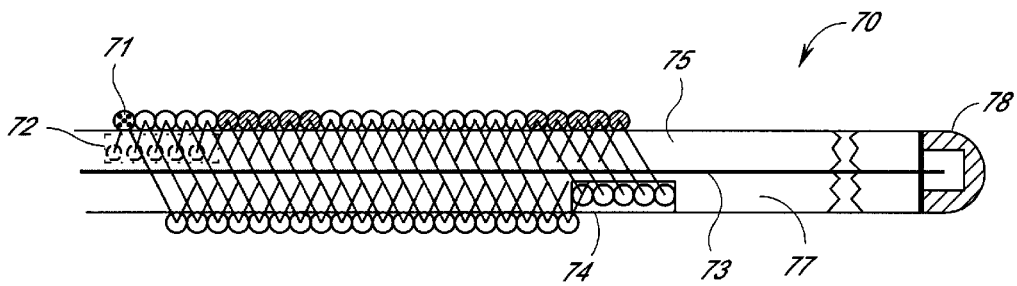
FIG. 6 is a schematic side view of an alternative filter device of the invention using bundles of hollow fiber dialysis membranes wound around a central dual lumen catheter.

FIG. 6 illustrates yet another filter device embodiment using bundles of hollow fiber dialysis membranes wound around a central dual lumen catheter. As shown, fiber bundle 71 may include up to five hollow fiber dialysis membranes of the type disclosed in the aforesaid patents, the descriptions of which are incorporated herein by reference. These fiber bundles comprise fibers which are uniformly and substantially parallel and wrapped around dual lumen catheter 70. The catheter includes an inflow lumen 75 which communicates with the membrane fiber bundles via an inflow header 72 with the opposite end of the dialysis membrane bundle connected to outflow lumen 77 via outflow header 74. A terminal header 78 is illustrated as is lumen separator panel 73. The number of the membrane bundle assemblies wound on the catheter may be selected to suit the needs of the patient in terms of the maximum toxin clearance specified in the patient's prescription.

Figure 7:
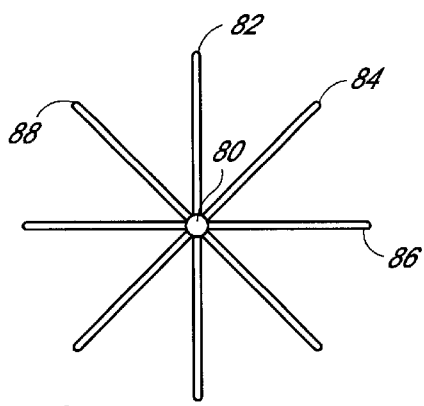
FIG. 7 is an end view of another filter device embodiment of the invention using dialysis membrane sheets.
Figure 8:
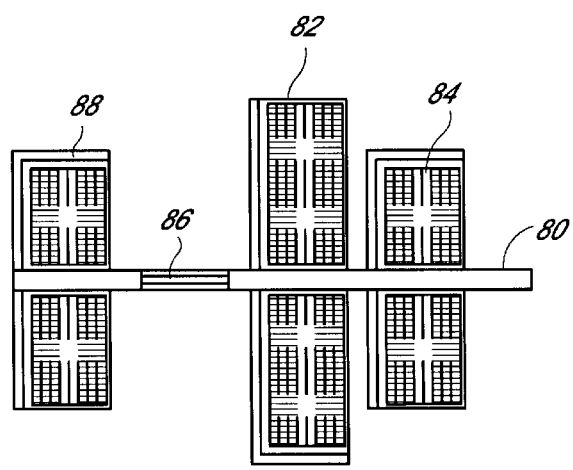
FIG. 8 is a side view of the assembly of FIG. 7.
Figure 9:
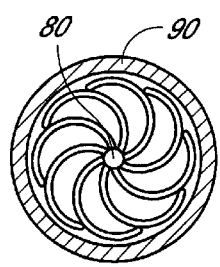
FIG. 9 schematically illustrates the device of FIG. 7 and 8 positioned within a blood vessel.

FIGS. 7, 8 and 9 illustrate yet another embodiment of a dialysis filter device formed of dialysis membrane sheets using segments which may be folded, creased or bonded along their edges to form a series of substantially flat or flattened envelopes of opposing sheets or portions of sheets which are secured to and extend radially from a multilumen catheter. In FIG. 7, an end view of such an assembly is illustrated and in FIG. 8, a side view showing panels 82, 84, 86 and 88 extending radially from catheter 80. Each panel is composed of an upper and lower or top and bottom dialysis membrane strip which is creased along the edge and bonded by suitable means such as heat sealing or adhesive. Within each of the membrane panels are inflow and outflow lumens as previously described in the systems as well as the filter embodiment in FIG. 4, whereby the dialysate fluid flows into and along the interior dialysate cavity for direct diffusive exposure to the patient's blood. The dialysate fluid containing diffused toxins is then directed out of the dialysate cavity. Blocks for diverting fluid flow may be placed in the inflow and outflow lumens of the catheter for directing dialysate through the respective lobe interior cavities. In FIG. 9, the filter device is illustrated within a blood vessel 90, and showing a preferred embodiment in which the length of the different panels or envelopes are somewhat greater than the radius of the blood vessel in which the assembly is implanted.

Figure 10:
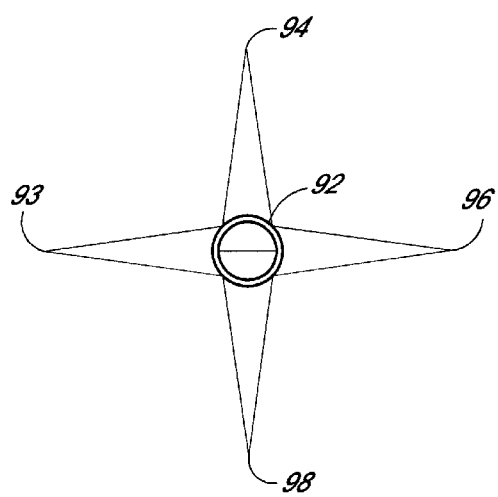
FIG. 10 is a schematic end view of a corrugated filter device embodiment of the invention.

FIG. 10 shows yet another embodiment of a dialysis filter device for providing a substantially large membrane surface to be exposed within the patient's blood vessel for increasing the rate of diffusion through the dialysis membrane. The efficiency of the elongated corrugated capsule of this embodiment may also be improved by twisting the capsule somewhat along its axis to present an angled membrane surface within the vessel thereby optimizing the shear rate of blood flow at the surface. The degree of twist may be determined and selected, depending on the number of lobes used, length of the capsule, cross-sectional dimension or depth of the lobes, blood flow, etc. as will be understood by those skilled in the art. Although four lobes are illustrated in the embodiment, any desired of lobes may be used, preferably up to about eight, depending on the selection of the capsule length, diameter, etc. to meet the patient's prescription and protocol.

Figure 11:
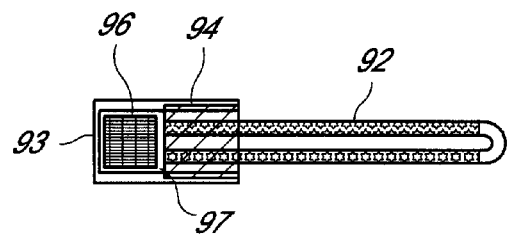
FIGS. 11 and 12 illustrate a plasma extraction capsule formed accoeding to the invention using both sheet membranes and hollow fiber membranes, FIG. 11 representing an end view of one lobe of such a device and FIG. 12 a side view thereof, the lobe being attached to a catheter.
Figure 12:
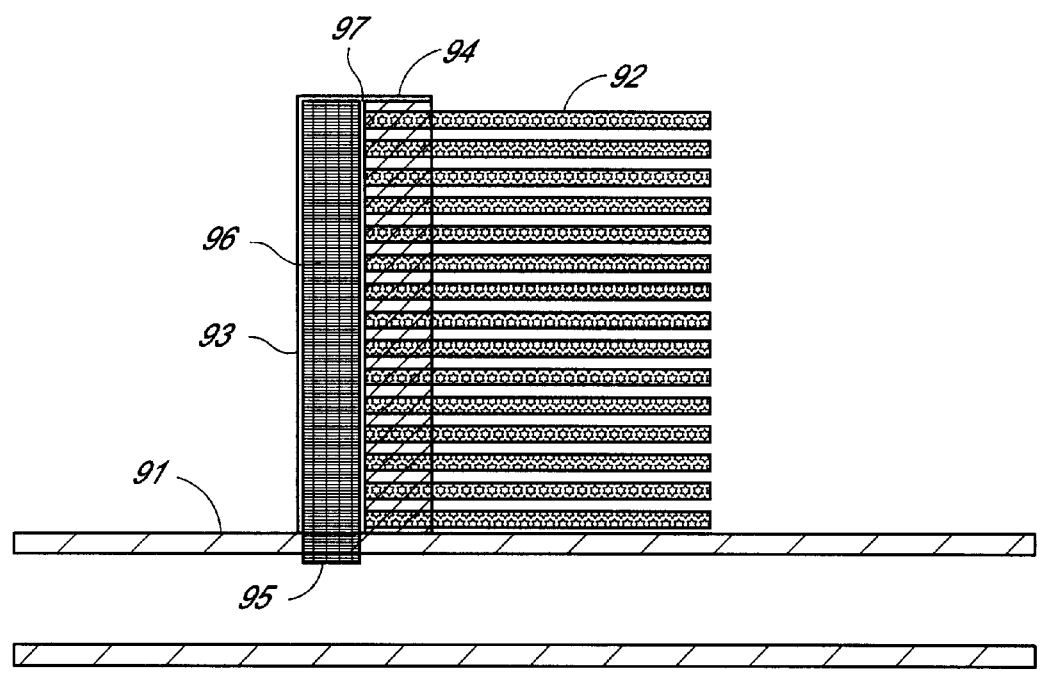

FIGS. 11 and 12 illustrate another preferred embodiment of a plasma extraction assembly using a combination of sheet membranes such a shown in FIGS. 7 and 8 and hollow fiber membranes. A plurality of hollow fiber membranes 92 are secured in a header 94 along the sheet membrane 96 to form the lobe 93 which is secured to and extends from catheter 91. The hollow fibers are fully described in U.S. Pat. No. 5,224,926 and 5,735,809. The hollow fiber membrane 92 is potted or otherwise bonded to the outer surface of a membrane sheet lobe, whereby the elongated axis of each of the hollow fibers preferably extends axially along the axis of the catheter 91. The fibers are shown extending from the leading edge 97 of the edge facing the blood flow in the vessel. As illustrated, each of the hollow fibers 92 is aligned so that both legs of the fiber are coaxial and coplanar with the elongated axis of the catheter 91, shown particularly in FIG. 12. However, the fibers need not be so aligned, and may be slanted, or even twisted somewhat along their respective axes such as described in U.S. Pat. No 5,375,809. The numbers of fibers used with each panel may also be varied, depending on the overall or total flat membrane and fiber surface to be exposed to the blood in the vessel. As previously described in FIGS. 7 and 8, the interior of each of the envelope lobes preferably contain a filler mesh strip or other flow directing component providing a fluid communication channel or cavity between the hollow fibers with the interior lumen of catheter 91. As shown in FIG. 12, the end 95 of sheet membrane 96 is secured in fluid communication with the lumen of catheter 91. Such a configuration allows for a blood plasma to diffuse through each of the hollow fiber membranes 92, into the interior passageway of the envelope or panel 96, and along the panel to the lumen of catheter 91 where the plasma is then directed ex vivo for plasma treatment.

The types of dialysis membranes, for optimal performance, must also be those available to take advantage of recent technological improvements and advanced biocompatible materials, including block co-polymers with surface enhancing end groups such as polyethylene-oxides which would eliminate the necessity of secondary biocompatible coatings. Solid state non-microporous membranes may be used as well as active element composite membranes. However, reference is also made to the materials disclosed in the aforesaid prior art which may be suitable for use as dialysis membrane materials, the selection of which will be understood in the art. Again, compatibility with the patient's blood and having pore size suitable for the appropriate dialysis and ultrafiltration functions is required for hemodialysis, well known to those skilled in the art, may be used.

The types and specifications of the membranes used in the dialysis elements of the invention including both hollow fiber and sheet membrane constructions such as transmembrane flux, sieving coefficients, etc. may be selected to meet the needs of different patient protocols as deemed optimal by the physician or caregiver. The area of membranes ($cm^2$) used and their sieving coefficients for reflecting the appropriate size and pores of the membranes and their distribution concentration, as well as the thickness, geometries and surface treatments may also be selected within the parameters known by those skilled in the art for dialysis membranes. In addition, the relative velocities between dialysate and blood which would be reflected in the flow rate of the dialysate in the circuit and consequently pass the membrane, may be considered as well as whether or not the dialysate is recycled or not prior to disposal. The blood velocity is fixed at a maximum by the location of the dialysis membrane in the vena cava, which is at a maximum of any venous blood in the body, thus insuring maximum constant driving force of toxin concentration for effective toxin diffusion and elimination, according to the invention.

The advantages of using the systems and methods of the present invention over the presently used hemodialysis techniques include reduction in risk of damage, infection or contamination of blood or blood components since no blood or plasma is removed from the patient's body. Thus, no blood, plasma or other blood components need to be returned to the body utilizing the methods and systems of the present invention thereby further reducing the potential for contamination or damage to the flood compartments. Moreover, there is a substantial reduction in the risk of infection to caregiver or patient from virus or bacteria utilizing a system of the invention. System simplification and components are also realized since only dialysate needs to be transported and controlled, resulting in reduction in weight, cost and complexity. The invention eliminates blood clotting in interior lumens of dialyzer cartridges. Continuous or near continuous operation also eliminates "peaks and valleys" in toxin concentrations, thereby improving the patient's feeling of general well-being throughout a substantially longer period of time as compared to presently used hemodialysis. The invention further eliminates traumatic shock to cardiovascular systems and other organs caused by massive fluid variations over short periods of time. The methods and system of the invention also control excess fluid volume on a continual basis rather than sporadically as is experienced in the traditionally and typically used systems. The systems of the present invention may be used for acute kidney failure in hospitals and chronic ESRD systems used in dialysis center or home-based operations and ambulatory portable operations for patients of all ages and economic status.

What is claimed is:

1. A method of removing toxins from a patient's blood without removing blood or blood plasma from a patient, said method comprising:

implanting a filter device within a blood vessel of a patient, said filter device comprising a dialysis membrane having an exterior surface for being exposed to the patient's blood and a dialysate cavity exposed to an interior surface of said dialysis membrane, continuously directing substantially uncontaminated or substantially decontaminated dialysate into said dialysate cavity and in diffusive communication with the patient's blood, dialyzing the patient's blood with said dialysate by diffusing toxins in the patient's blood into said dialysate, and continuously removing toxin contaminated dialysate from said filter device without removing blood or blood plasma from the patient.

2. A method of claim 1 including providing a multiple lumen catheter in fluid communication with said dialysate cavity for directing said dialysate thereto and therefrom.

3. A method of claim 2 wherein said filter device includes an ultrafiltration membrane having an exterior surface for being exposed to said patient's blood and an ultrafiltration cavity exposed to an interior surface of said ultrafiltration membrane.

4. A method of claim 3 wherein said catheter comprises a first and second lumen each in fluid communication with said dialysate cavity,and a third lumen in fluid communication with said ultrafiltration cavity for directing ultrafiltrate therefrom.

5. A method of claim 4 including selectively pumping ultrafiltrate from said ultrafiltration cavity.

6. A method of claim 1 wherein said filter device includes an ultrafiltration membrane having an exterior surface for being exposed to said patient's blood and an ultrafiltration cavity exposed to an interior surface of said ultrafiltration membrane.

7. A method of claim 1 including recovering said toxin contaminated dialysate from said filter device, absorbing toxins from said contaminated dialysate to produce substantially decontaminated dialysate, and directing said substantially decontaminated dialysate filter device.

8. A method of claim 1 wherein dialysate is directed into said filter device using gravity feed.

9. A method of claim 8 wherein contaminated dialysate is siphoned gravitationally from said filter device.

10. A method of claim 8 including selectively pumping contaminated dialysate from said filter device.

11. A method of claim 1 wherein dialysate is pumped into the dialysate cavity of said filter device from a dialysate supply source.

12. A method of claim 11 wherein contaminated dialysate is pumped from said filter device.

13. A method of claim 12 including using a microprocessor controller for controlling the flow of dialysate to and from said filter device.

14. A method of claim 13 including sensing the pressure of dialysate pumped to and from said filter device and controlling the flow of dialysate in response to the sensed dialysate pressure.

15. A method of claim 14 including sensing the blood urea nitrogen level of the dialysate removed from the filter device.

16. A method of claim 12 wherein said filter device includes an ultrafiltration membrane having an exterior surface for being exposed to said patient's blood and an ultrafiltration cavity exposed to an interior surface of said ultrafiltration membrane, including selectively pumping ultrafiltrate from said ultrafiltration cavity and using a microprocessor controller for controlling said pumping.

17. A method of claim 1 including filtering toxins from dialysate directed to said dialysate cavity.

18. A method of claim 1 including filtering bacteria from dialysate directed to and from said filter device.

19. A method of claim 18 including sensing the blood urea nitrogen level of the dialysate removed from the filter device.

20. A method of claim 1 including sensing the blood urea nitrogen level of the dialysate removed from the filter device.

21. A method of claim 1 wherein said substantially uncontaminated or substantially decontaminated dialysate is gravitationally fed to said filter device.

22. A method of claim 1 wherein said toxin contaminated dialysate is removed from said filter device by siphoning.

23. A method of claim 22 wherein said siphoning is carried out by providing an outflow tubing having a one-way valve.

24. A method of claim 23 including providing manual vacuum in said outflow tubing.

25. A method of claim 1 wherein said dialysis membrane has a low flux dialyser cut-off of about $5 \times 10^3$ daltons and a high flux cut-off of about $5 \times 10^4$ daltons.

26. A method of claim 1 or 25 wherein said dialysis membrane comprises one or more microporous membrane sheets.

27. A method of claim 1 or 25 wherein said dialysis membrane comprises a plurality of elongated hollow microporous membrane filters.

28. Apparatus for removing toxins from a patient's blood comprising:
- a filter device for being implanted in a patient's blood vessel comprising a dialysis membrane having an exterior surface for being exposed to a patient's blood and a dialysate cavity exposed to an interior surface of said dialysis membrane for receiving dialysate fluid directed thereto from a dialysate supply source and whereby said dialysate fluid is in direct diffusive communication with a patient's blood,
- a multiple lumen catheter secured to said filter device and in fluid communication with said dialysate cavity and having a first lumen for directing fresh dialysate thereto from a dialysate supply source and a second lumen for directing toxin contaminated dialysate, therefrom, and
- a dialysate supply source in fluid communication with said catheter capable of continuously supplying fresh dialysate to said dialysate cavity.

29. An apparatus of claim 28 including a first dialysate pump cooperating with said first lumen and a second dialysate pump cooperating with said second lumen.

30. An apparatus of claim 29 including a microprocessor-controller cooperating with said first and second dialysis pumps for controlling the operation of said pumps.

31. An apparatus of claim 30 including one or more pressure transducers cooperating with said multiple lumen catheter for sensing the flow rate of dialysate fluid therein and communicating with said microprocessor-controller.

32. An apparatus of claim 31 comprising one or more first pressure transducers cooperating with said first lumen and one or more second pressure transducers cooperating with said second lumen.

33. An apparatus of claim 30 including a blood toxin sensor cooperating with said second lumen for sensing the concentration of toxins in the dialysate directed from said filter device, and wherein said sensor is in communication with said microprocessor-controller.

34. An apparatus of claim 28 wherein said filter device includes an ultrafiltration membrane having an exterior surface for being exposed to a patient's blood and an ultrafiltration cavity exposed to an interior surface of said ultrafiltration membrane.

35. An apparatus of claim 34 wherein said multiple lumen catheter comprises a third lumen for directing ultrafiltrate from said ultrafiltration cavity and an ultrafiltration pump cooperating with said third lumen.

36. An apparatus of claim 34 including a microprocessor-controller cooperating with said first and second dialysate pumps and said ultrafiltration pump for controlling the operation of said pumps.

37. An apparatus of claim 36 including one or more pressure transducers cooperating with said multiple lumen catheter and in communication with said microprocessor-controller.

38. An apparatus of claim 37 comprising one or more first pressure transducers cooperating with said first lumen, one or more second pressure transducers cooperating with said second lumen and one or more third pressure transducers cooperating with said third lumen, wherein said transducers are in flow rate sensing communication with said respective lumens.

39. An apparatus of claim 35 including a receptacle for cooperating with said third lumen for receiving ultrafiltrate.

40. An apparatus of claim 34 wherein said ultrafiltration membrane has a cut-off of about $5.8 \times 10^4$ daltons.

41. An apparatus of claim 28 including a toxin absorption device cooperating with said dialysate supply source for substantially filtering toxins directed to said filter device.

42. An apparatus of claim 28 wherein said second lumen directs dialysate fluid from said filter device to said dialysate supply source, and wherein said apparatus includes a toxin absorption device cooperating with said first lumen for substantially filtering toxins from dialysate directed to said filter device from said dialysate supply source.

43. An apparatus of claim 28 wherein said dialysate supply source comprises substantially toxin free dialysate and wherein said apparatus includes a receptacle cooperating with said second lumen for receiving said toxin containing dialysate.

44. An apparatus of claim 43 including a tube in communication with said second lumen of said catheter for directing toxin containing dialysate to said receptacle, and a one-way valve cooperating with said tube for preventing fluid flow from said tube to said catheter.

45. An apparatus of claim 44 including a vacuum pump cooperating with said tube or said receptacle for creating a vacuum in said tube for initiating fluid flow therethrough.

46. An apparatus of claim 45 wherein said vacuum pump comprises a hand vacuum pump and one or more check valves.

47. An apparatus of claim 43 including a flow control valve cooperating with said tube.

48. An apparatus of claim 43 including a siphon device for creating a vacuum in said tube for initiating and maintaining fluid flow therethrough.

49. An apparatus of claim 28 wherein said filter device comprises a first dialysate cavity exposed to an interior surface of a first portion of said dialysis membrane and a second dialysate cavity exposed to an interior surface of a second portion of said dialysis membrane, and a partition separating said first and second dialysate cavities.

50. An apparatus of claim 49 wherein said first lumen of said multiple lumen catheter is in fluid communication with said first dialysate cavity, and said second lumen of said multiple lumen catheter is in fluid communication with said second dialysate cavity.

51. An apparatus of claim 50 wherein said filter member includes a third cavity having an inlet port communicating with said multiple lumen catheter and an outlet port communicating with the exterior of said filter device.

52. An apparatus of claim 51 wherein said multiple lumen catheter includes a third lumen communicating with said inlet port of said third cavity.

53. As apparatus of claim 50 wherein said first dialysate cavity is in fluid communication with said second dialysate cavity.

54. An apparatus of claim 49 wherein said first dialysate cavity is in fluid communication with said second dialysate cavity.

55. An apparatus of claim 49 wherein said filter device comprises a first elongated assembly having a first cross-sectional dimension and a second elongated assembly having a cross-sectional dimension.

56. An apparatus of claim 55 wherein said dialysis membrane comprises a first portion enveloping said first elongated assembly and a second portion enveloping said second elongated assembly.

57. An apparatus of claim 56 wherein said first and second elongated assemblies are substantially coaxial.

58. An apparatus of claim 57 wherein said first and second elongated assemblies are substantially cylindrical and wherein said first and said second dialysate cavities are substantially semi-cylindrical and extend along opposite sides of said first and second elongated assemblies, respectively.

59. An apparatus of claim 28 wherein said filter device comprises a plurality of elongated dialysis membrane fibers having a hollow interior defining said dialysate cavity.

60. An apparatus of claim 28 wherein said filter device comprises a corrugated tube formed by one or more sheets of said dialysis membrane.

61. An apparatus of claim 60 wherein said corrugated tube comprises grooves and ridges formed along said dialysis membranes sheet.

62. An apparatus of claim 61 wherein said grooves and ridges form a plurality of lobes.

63. An apparatus of claim 59 wherein said plurality of fibers comprises a bundle of substantially parallel fibers.

64. An apparatus of claim 63 wherein said filter device comprises a plurality of helically wound bundles.

65. An apparatus of claim 59 wherein said filter device comprises:
a dual lumen catheter segment having a first lumen for directing dialysate to said dialysate membrane fibers and a second lumen for receiving dialysate from said dialysate membrane fibers.

66. An apparatus of claim 28 wherein said fiber device comprises a cylindrical tube formed by one or more sheets of said dialysis membrane.

67. An apparatus of claim 66 wherein said filter device comprises a plurality of capsules, each capsule comprising an envelope formed of panels of said dialysis membrane sheets.

68. An apparatus of claim 27 wherein said filter device comprises a dual lumen catheter segment having a first lumen for directing dialysate to said capsules and as second lumen for receiving dialysate from said capsules, and wherein said capsules extend radially from said catheter segment.

69. An apparatus of claim 28 wherein said dialysate supply source is a gravity feed supply source.

70. An apparatus of claim 28 wherein said dialysis membrane has a low flux dialyser cut-off of about $5\times10^3$ and a high flux cut-off of about $5\times10^4$ daltons.

71. An apparatus of claims 28, 56, 58, 59, 66, 62, 70 or 40 wherein said dialysis membrane comprises a microporous membrane.

72. An apparatus of claim 71 wherein said dialysis membrane comprises one or more microporous membrane sheets.

73. An apparatus of claim 71 wherein said dialysis membrane comprises a plurality of elongated hollow microporous membrane fibers.

74. An apparatus of claim 71 wherein said microporous membrane comprises a combination of one or more microporous membrane sheets and a plurality of elongated hollow microporous membrane fibers.

* * * * *